United States Patent [19]

Samuels et al.

[11] Patent Number: 5,455,045
[45] Date of Patent: Oct. 3, 1995

[54] HIGH DOSE FORMULATIONS

[75] Inventors: Glenn J. Samuels, Sunnyvale; Jung-Chung Lee, San Jose; Charles Lee, Union City; Stephen Berry, Saratoga; Paul J. Jarosz, Los Altos, all of Calif.

[73] Assignee: Syntex (U.S.A.) Inc., Palo Alto, Calif.

[21] Appl. No.: 61,656

[22] Filed: May 13, 1993

[51] Int. Cl.$^6$ ............................................. A61K 9/48
[52] U.S. Cl. ......................... 424/451; 424/489; 264/4.1
[58] Field of Search ................. 544/153; 260/210; 424/451, 489; 264/4.1

[56] References Cited

U.S. PATENT DOCUMENTS

| | | | |
|---|---|---|---|
| 3,374,146 | 3/1968 | Blicharz et al. | 167/83 |
| 3,705,946 | 12/1972 | Dyke | 424/279 |
| 3,853,919 | 12/1974 | Mori et al. | 260/343.3 |
| 3,903,071 | 9/1975 | Holmes | 260/210 |
| 4,002,718 | 1/1977 | Gardella et al. | 424/37 |
| 4,820,523 | 4/1989 | Shtohryn et al. | 424/469 |
| 4,842,865 | 6/1989 | Durr et al. | 424/456 |
| 4,894,235 | 1/1990 | Kohne et al. | 424/452 |
| 4,936,074 | 6/1990 | Graham | 53/440 |
| 5,247,083 | 9/1993 | Knox et al. | 544/153 |

FOREIGN PATENT DOCUMENTS

| | | | |
|---|---|---|---|
| 0713293A2 | 3/1986 | European Pat. Off. | A61K 31/445 |
| 1572226 | 7/1980 | United Kingdom | A61K 9/48 |

OTHER PUBLICATIONS

Ewart T. Cole, "Liquid–Filled Hard–Gelatin Capsules", Pharm. Technol. 13 (9), 124–140 (1989).

Howard, et al., "Drug Release From Thermosetting Fatty Vehicles Filled Into Hard Gelatin Capsules", Drug Dev. & Indust. Phar., 13(6), 1031–1045 (1987).

Thomas, et al., "The Use of Xylitol as a Carrier for Liquid–Filled Hard–Gelatin Capsules", Pharm. Technol. Int. 36–40, Oct. 1991.

McTaggart, et al., "The evaluation of an automatic system for filling liquids into hard gelatin capsules", J. Pharm. Pharmacol. 1984,36: 119–121.

Smith, et al., "The filling of molten ibuprofen into hard gelatin capsules", Int. J. of Pharmaceutics, 59 (1990) 115–119.

Walker, et al., "The filling of molten and thixotropic formulations into hard gelatin capsules", J. Pharm. Pharmacol. 1980, 32: 389–393.

*Primary Examiner*—Thurman K. Page
*Assistant Examiner*—William E. Benston, Jr.
*Attorney, Agent, or Firm*—Pauline Ann Clarke; Theodore J. Leitereg; Alan M. Krubiner

[57] ABSTRACT

Mycophenolate mofetil and mycophenolic acid can be conveniently manufactured into high dose oral formulations by the hot melt filling of a supercooled mycophenolate mofetil or mycophenolic acid liquid into a pharmaceutical dosage form. High dose oral pharmaceutical formulations and manufacturing methods therefor are disclosed.

6 Claims, No Drawings

HIGH DOSE FORMULATIONS

FIELD OF THE INVENTION

The present invention relates to mycophenolate mofetil and mycophenolic acid, particularly to improved formulations thereof, and specifically to high dose formulations. The invention is also directed to methods of manufacturing the formulations.

BACKGROUND INFORMATION

Mycophenolic acid ("MPA") was initially described as a weakly-active antibiotic found in the fermentation broth of *Penicillium brevicompactum*, having the following structure.

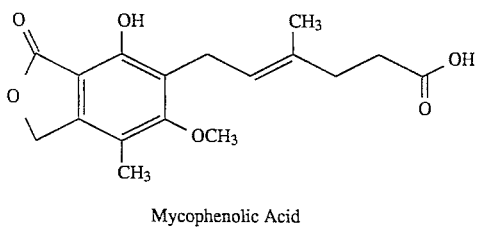

Mycophenolic Acid

MPA and certain related compounds, such as mycophenolate mofetil (the morpholinoethyl ester of MPA), having the following structure:

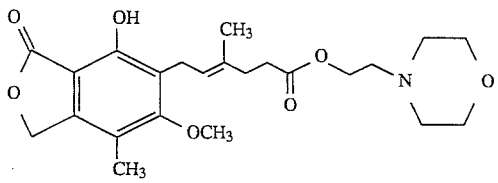

have more recently been described as having particularly advantageous therapeutic properties, e.g., as immunosuppressant drugs. See, for example, U.S. Pat. Nos. 3,880,995; 4,727,069; 4,753,935; and 4,786,637, all incorporated herein by reference.

MPA and mycophenolate mofetil, notwithstanding the improved oral bioavailability characteristics of the latter, require daily doses on the order of 2.0 to as much as 3.5 or 4.0 grams per day (or even 5.0 grams per day in the case of MPA, for example as described in U.S. Pat. No. 3,880,995) depending upon the patient and the disease state being treated. Using a conventional dosage formulation containing 250 mg in a standard size 1 (0.48 cc volume) capsule, a patient receiving a 3.0 gram daily dose is required to take twelve capsules each day, giving rise to patient convenience and compliance concerns. It has remained desired to provide high dose oral formulations for MPA and mycophenolate mofetil, particularly in view of their relatively high daily doses.

The filling of molten or thixotropic liquids and pastes into hard gelatin capsules has been described as a way of reducing the problems of conventional pharmaceutical processing methods, and adaptations of capsule filling machines for this purpose have been described in the literature. See, e.g., Walker, et al., "The filling of molten and thixotropic formulations into hard gelatin capsules," *J.Pharm.Pharmacol.*, Vol. 32, 389–393 (1980); and McTaggart, et al., "The evaluation of an automatic system for filling liquids into hard gelatin capsules," *J.Pharm.Pharmacol.*, Vol. 36, 119–121 (1984). The advantages of this formulation technology have been described as including "low content uniformity variation, reduced dust generation giving rise to reduced cross contamination hazards, controlled dissolution rate using solid solution or slow release systems, the ability to process low melting point or liquid drugs and the possibility of in-house formulation development and manufacture" (McTaggart, et al., at page 119). Liquid-filled hardgelatin capsule formulations have been particularly suggested for "drugs that have low melting points, drugs that are low-dosed or that are oxygen- or moisture-labile, and drugs that require bioavailability enhancement" including "the development of sustained-release formulations." Cole, "Liquid-Filled Hard Gelatin Capsules," *Pharm. Technol.*, Vol. 13, No. 9, 134–140 at 134 (1989).

More recently, a new aspect of liquid-paste filling was reported "whereby a high fill weight of a low-melting thermostable drug (ibuprofen) can be attained using low levels of excipient whilst preserving the facility to obtain a wide range of drug release rates." Smith, et al., "The filling of molten ibuprofen into hard gelatin capsules," *Int. J. Pharm.*, Vol. 59, 115–119 at 115 (1990). There, ibuprofen (m.p. 77° C.) was heated to 70°–80° C., alone and with a variety of excipients, and filled into a variety of capsule sizes. Maximum approximate fill weights for ibuprofen alone, of 450 mg (size 1), 605 mg (size 0), 680 mg (size 0 elongated), and 825 mg (size 00), were reported.

Mycophenolate mofetil has a melting point of 95° C. MPA has a melting point of 141° C. Neither is a low-melting drug that would be considered suitable for hot melt filling, particularly given an upper fill temperature of 80° C., preferably below 60° C., for hard gelatin capsules due to their own melting characteristics. It was surprisingly discovered that mycophenolate mofetil, once heated above its melting point, has the unexpected property of remaining liquid for sustained periods of time after cooling to significantly lower temperatures. Such a considerable delay in solidification even after cooling below melting point (a "supercooling" phenomena) was reported as "a problem" to be overcome in the preparation of medications in the form of pearls (see U.S. Pat. No. 5,188,838).

In the present invention, mycophenolate mofetil's ability to be supercooled has been extended by the application of that discovery to hot melt filling, to produce previously unattainable high dose formulations. It has also been discovered that MPA exhibits the ability to be supercooled, and while the duration is shorter than that measured for mycophenolate mofetil, MPA's supercooling duration is sufficient for producing previously unattainable high dose formulations.

SUMMARY OF THE INVENTION

It has surprisingly been discovered that mycophenolate mofetil and MPA can be conveniently manufactured into high dose oral formulations by the hot melt filling of a supercooled mycophenolate mofetil or MPA liquid into a pharmaceutical dosage form.

One aspect of the invention relates to a pharmaceutical formulation having a therapeutically effective amount of mycophenolate mofetil, the mycophenolate mofetil having been liquefied by heating to a first temperature above about 95° C., then cooled to a second temperature below about 80° C. at which the mycophenolate mofetil remained liquefied, followed by filling the mycophenolate mofetil into a pharmaceutical dosage form while in said cooled liquefied state. In a preferred embodiment, the formulation includes a disintegrant such as croscarmellose sodium.

In another aspect, the invention relates to high dose formulations of mycophenolate mofetil, having 500 mg in a size 1 capsule, 750 mg in a size 0 capsule, or 1000 mg in a size 00 capsule.

Still another aspect of the invention relates to methods for manufacturing a pharmaceutical formulation of MPA or mycophenolate mofetil, including the steps of:

liquefying the active agent by heating it to a first temperature above its melting point;

cooling the liquefied active agent to a second temperature below its melting point, at which second temperature the active agent remains liquefied; and filling the liquefied active agent into a pharmaceutical dosage form.

In a preferred aspect, the manufacturing method includes the steps of:

liquefying mycophenolate mofetil by heating it to a temperature above about 95° C. (preferably to about 95°–120° C.);

admixing croscarmellose sodium, in an amount sufficient to serve as a dispersant in the formulation when finished, with the liquefied mycophenolate mofetil;

cooling the admixed liquefied mycophenolate mofetil and croscarmellose sodium to a temperature below about 80° C. (preferably below about 60° C.); and filling the cooled, liquefied mycophenolate mofetil admixed with croscarmellose sodium into hard or soft capsules.

DETAILED DESCRIPTION OF THE INVENTION

Definitions and General Parameters

The following definitions are set forth to illustrate and define the meaning and scope of the various terms used to describe the invention herein.

Reference to the active agent employed in the formulations of the present invention, "mycophenolate mofetil," is intended to include the pharmaceutically acceptable salts thereof.

The size and volume of the capsules employed in the formulations of the present invention include the following:

| SIZE | VOLUME |
|------|--------|
| 1    | 0.48 cc |
| 0    | 0.67 cc |
| 0 EL | 0.74 cc |
| 00   | 0.95 cc | as described in the Shinogi (formerly Elanco) Qualicaps capsule Technical Information Manual (F6.200, p. 10).

Materials

Mycophenolate mofetil can be made as described in U.S. Pat. No. 4,753,935, previously incorporated by reference. Mycophenolic acid is commercially available, e.g., from Sigma Chemical Company, St. Louis, Mo. Pharmaceutically acceptable excipients, hard and soft gelatin capsules, cellulosic capsules (also referred to as starch based capsules, commercially available from Warner Lambert) and capsule filling machinery are commonly commercially available.

Formulations

Mycophenolate mofetil or MPA can be employed as the active agent in the formulations of the present invention, either alone or in combination with pharmaceutically acceptable excipients and/or other medical agents. Generally, the formulation will contain about 90% to 100%, preferably about 95% to 96% by weight of active agent, the remainder being suitable pharmaceutical excipients, carriers, etc, preferably about 4% by weight of a disintegrant (most preferably croscarmellose sodium).

Normally employed excipients include, for example, disintegrants (such as croscarmellose sodium, sodium carboxymethylcellulose, crosspovidone, sodium starch glycolate or the like), diluents (such as lactose, sucrose, dicalcium phosphate, or the like), lubricants (such as magnesium stearate or the like), binders (such as starch, gum acacia, gelatin, polyvinylpyrrolidine, cellulose and derivatives thereof, and the like), viscosity aids (such as cellulose) and crystal modifying aids (such as sodium chloride). A crystal retardant or poison [such as sorbitol 5–7% w/w (e.g., as described by Thomas, et al., "The Use of Xylitol as a Carrier for Liquid-Filled Hard-Gelatin Capsules," *Pharm. Tech. Int.*, vol. 3, 36, 38–40 (1991) incorporated herein by reference) hydroxypropylmethyl cellulose, or hydroxypropylcellulose] can be added to an active agent that exhibits supercooling (stays liquid below its melting temperature) for a time period less than that optimally desired for dosage form filling, for example prior to or after the active agent has been liquefied.

The mycophenolate mofetil formulations of the invention have a therapeutically effective amount of mycophenolate mofetil, the mycophenolate mofetil having been liquefied by heating to a first temperature above about 95° C., then cooled to a second temperature below about 80° C. at which the mycophenolate mofetil remained liquefied, followed by filling the mycophenolate mofetil into a pharmaceutical dosage form, such as a capsule (e.g., a hard gelatin capsule, a soft gelatin capsule, or a cellulosic capsule) or a tablet mold (e.g., by injection molding) while in said cooled liquefied state. Tablets formulations of the invention are preferably coated with a pharmaceutically acceptable coating material (such as opadry, commercially available from Coloron, Inc. of West Point, Pa.) for example by spray coating or other coating methods conventionally employed in the field.

In a preferred embodiment, particularly for capsules, the formulations include croscarmellose sodium, admixed with liquefied mycophenolate mofetil prior to cooling in an amount sufficient to serve as a disintegrant.

Preferred formulations include mycophenolate mofetil (95–100% w/w, most preferably 96% w/w) and croscarmellose sodium (0–5% w/w, most preferably 4% w/w), filled into a gelatin capsule.

Manufacturing Methods

The methods for manufacturing a pharmaceutical formulations of include the steps of:

liquefying the active agent by heating it to a first temperature above its melting point;

cooling the liquefied active agent to a second temperature below its melting point, the active agent remaining liquefied at the second temperature; and filling the liquefied active agent into a pharmaceutical dosage form.

Once filled, the liquefied active agent is allowed to solidify.

A preferred manufacturing method, where the active agent is mycophenolate mofetil, includes the steps of:

liquefying mycophenolate mofetil by heating it to a temperature above about 95° C. (preferably about 95° to 120° C.);

admixing croscarmellose sodium (in an amount sufficient to serve as a disintegrant in the formulation when finished) with the liquefied mycophenolate mofetil;

cooling the admixed liquefied mycophenolate mofetil and croscarmellose sodium to a temperature below about 80° C. (preferably below about 60° C., most preferably about 35° to 45° C.); and filling the cooled, liquefied mycophenolate mofetil admixed with croscarmellose sodium into hard or soft capsules (preferably using temperature controlled filling apparatus adjusted to the temperature of the cooled admixture).

The cooling and mixing rates can be optimized depending upon the particular active agent, manufacturing process, size and equipment employed. While the underlying theory for formulating supercooled liquids is not completely understood (for example, it remains unpredictable whether a given active agent will exhibit supercooling at all, as illustrated below in Example 6), particularly for larger scale manufacturing processes, some factors to be considered include stirring rate (e.g., for mycophenolate mofetil it can be advantageous to avoid causing sheer forces when stirring, or to eliminate stirring altogether), stirring equipment (e.g., overhead or magnetic bar), cooling rate, cooling temperature, and filling equipment temperature.

Formulations prepared by the above-described process of the invention may be identified by the solid (as opposed to compacted powder or granule) contents of a capsule. For example, mycophenolate mofetil forms a friable, solid, off-white mass when cooled in a capsule. The presence of such a solid mass is a method of detecting a formulation made by the invention and/or use of a process of the invention.

Preferred Processes

In a presently preferred process, mycophenolate mofetil is liquefied by heating it to a temperature above about 95° C.; croscarmellose sodium is admixed with the liquefied mycophenolate mofetil in an amount sufficient to serve as a disintegrant in the formulation when finished; the admixed liquefied mycophenolate mofetil and croscarmellose sodium are cooled to a temperature below about 80° C. (most preferably below about 60° C.); and the cooled, liquefied mycophenolate mofetil admixed with croscarmellose sodium is filled into hard or soft capsules.

Preferred Formulations

Presently preferred is the formulation of 96% w/w mycophenolate mofetil and 4% w/w croscarmellose sodium, most preferably in a size 1 hard gelatin capsule containing 500 mg active ingredient, in a size 0 hard gelatin capsule containing 750 mg active ingredient, or in a size 00 hard gelatin capsule containing 1000 mg active ingredient.

Administration

The formulation of the present invention are useful for oral administration in any oral treatment regimen for MPA or mycophenolate mofetil. While human dosage levels have yet to be finalized, generally, a daily dose of mycophenolate mofetil or mycophenolic acid is from about 2.0 to 5.0 grams, preferably about 2.0 to 3.5 grams. The amount of active compound administered will, of course, be dependent on the subject and disease state being treated, the severity of the affliction, the manner and schedule of administration and the judgment of the prescribing physician. For example, a treatment regimen for administering 3.0 grams of mycophenolate mofetil per day, which previously entailed taking 6 size 1 capsules (250 mg) twice daily, when administered with a formulation of the present invention entails taking 2 size 0 capsules (750 mg) twice daily.

EXAMPLES

The following examples are given to enable those skilled in the art to more clearly understand and to practice the present invention. They should not be considered as limiting the scope of the invention, but merely as being illustrative and representative thereof.

Example 1

Mycophenolate mofetil (50 g) was added to a 250 ml beaker and melted on a hot plate at low setting. The molten material was allowed to cool to 40°–50° C., at which temperature it remained a liquid, which was drawn into a 20 ml disposable syringe using the plunger. The syringe was used to fill the body of a size 0 hard gelatin capsule using the luer connection as a fill nozzle. The material was dispensed bottom up, withdrawing the nozzle as fill proceeded. The capsule cap was then placed on the filled body and the closed capsule allowed to stand overnight, to give a high dose mycophenolate mofetil capsule.

The above-described procedure can be used to produce batches of 20 to 30 size 0 high dose capsules of mycophenolate mofetil.

Example 2

This example illustrates the preparation of a 2.0 kg batch of a representative high dose pharmaceutical formulation for oral administration containing mycophenolate mofetil as the active compound.

Mycophenolate mofetil (1920 g; 96% w/w) is added to a jacketed kettle. The temperature is raised to a temperature between 95° and 120° C. Croscarmellose sodium (80 g; 4% w/w) is added to the jacketed kettle with mixing. The temperature is lowered to a temperature between 35° and 45° C., with continued mixing. The cooled mixture (750 mg) is filled into the bodies of 2,500 size 0 hard gelatin capsules (allowing for a small amount of surplus), the temperature of the filling apparatus being adjusted to between 35° and 45° C.

Example 3

Alternative Dosage Forms

Soft Capsules

By following the procedure of Example 1 or 2, and substituting soft gelatin capsules for the hard gelatin capsules there-employed and using the rotary die filling process, there are obtained the corresponding soft-gelatin capsule dosage forms.

Cellulosic Capsules

By following the procedure of Example 1 or 2, and substituting cellulosic capsules for the hard gelatin capsules there-employed and cooling the molten material to 80° C., there are obtained the corresponding cellulosic capsule dosage forms.

EXAMPLE 4

Mycophenolic acid 90% w/w (90 g) is added to a 500 ml beaker and melted of a hot plate at a temperature of 145° C. To the molten material is added croscarmellose sodium 4% w/w (4 g) and sorbitol 6% w/w (a 70% solution, added dropwise) with gentle mixing. The mixture is allowed to cool to 50°–60° C., at which temperature it remains a liquid, which is drawn into a 20 ml disposable syringe using the plunger. The syringe is used to fill the body of a size 0 hard gelatin capsule using the luer connection as a fill nozzle. The capsule cap is then placed on the filled body and the closed capsule allowed to stand overnight, to give a high dose mycophenolic acid capsule.

Example 5

Determination of Average and Maximum Fill Weight For Different Capsule Sizes Mycophenolate mofetil hard gelatin capsule formulations were manufactured according to the procedures described in Example 1 and filled into hard gelatin capsules of various sizes. The average (n=6) and maximum fill weights for each size were calculated, and are reported below.

| SIZE | VOLUME | AV. FILL | MAX. FILL |
| --- | --- | --- | --- |
| 1 | 0.48 cc | 508 mg | 580 mg |
| 0 | 0.67 cc | 767 mg | 810 mg |
| 0 EL | 0.74 cc | n/a | 890 mg |
| 00 | 0.95 cc | 1037 mg | 1080 mg |

The formulations of the present invention contained significantly more mycophenolate mofetil per capsule (1058 mg/cc) than did conventional formulations such as 250 mg of mycophenolate mofetil in a size 1 capsule (520 mg/cc).

Example 6

Supercooling Test

Mineral oil (15 ml) in a 50 ml beaker is heated to a predetermined temperature in excess of the melting point of the compound to be tested, using a hotplate. A 2–5 g sample of test compound (a solid at room temperature) is weighed into a scintillation vial, and the vial is placed into the preheated mineral oil. The test compound is allowed to melt, after which the scintillation vial is removed from the mineral oil and allowed to return to room temperature. Changes in the appearance of the test compound, including recrystallization, and the time before solidification are recorded.

When mycophenolate mofetil (m.p. 95° C.) was employed as the test compound in the above procedure, and heated to 120° C., the compound remained a liquid at room temperature for up to two hours. Mycophenolate mofetil, heated to melting and filled into size 0 capsules, recrystallized in the capsule to form a solid mass when stored at room temperature conditions for approximately 12 hours.

Mycophenolic acid (m.p. 141° C.), when tested in the above procedure and heated to melting, after cooling to room temperature did not exhibit crystal seed nucleation for about ten minutes, and remained a liquid for 35 minutes prior to complete recrystallization. Mycophenolic acid plus one drop of a 70% solution of sorbitol (about 7% wt/wt) when tested in the above procedure and heated to melting, after cooling to room temperature did not exhibit crystal seed nucleation for about ten minutes, and remained a liquid for over 1 hour.

Similarly, when tested in the above procedure and heated to 120° C.:

trenbelone acetate (m.p. 97° C.), methocarbamol (m.p. 94° C.) and captopril (m.p. 87°/104° C.) remained a liquid at room temperature for at least two hours;

gemfibrozil (m.p. 58° C.), guaifenesin (m.p. 79° C.), flurbiprofen (m.p. 110° C.), and flutamide (m.p. 112° C.) remained a liquid for about 10 minutes; and nabumetone (m.p. 80) recrystallized immediately.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for manufacturing a pharmaceutical formulation having an active agent selected from the group consisting of mycophenolate mofetil and mycophenolic acid, comprising the steps of:

liquefying the active agent by heating it to a first temperature above its melting point;

cooling said liquefied active agent to a second temperature below its melting point, at which second temperature said active agent remains liquefied; and filling said liquefied active agent into a pharmaceutical dosage form.

2. The method of claim 1 wherein said pharmaceutical dosage form is a capsule.

3. The method of claim 2 wherein said second temperature is lower than the melting point of said capsule.

4. The method of claim 1 further comprising the step of admixing a second material with said active agent, said second material being a second active agent or a pharmaceutically acceptable excipient; wherein said liquefying step comprises heating said admixed active agent and second material to a temperature at least above the melting point of said active agent and optionally above the melting point of said second material.

5. A method for manufacturing a pharmaceutical formulation having mycophenolate mofetil as an active agent comprising the steps of:

liquefying mycophenolate mofetil by heating it to a temperature of about 95° to 120° C.;

admixing croscarmellose sodium, in an amount sufficient to serve as a disintegrant in said formulation when finished, with said liquefied mycophenolate mofetil;

cooling said admixed liquefied mycophenolate mofetil and croscarmellose sodium to a temperature below about 80° C.; and filling said cooled, liquefied mycophenolate mofetil admixed with croscarmellose sodium into hard or soft gelatin capsules.

6. The method of claim 5 wherein said admixed liquefied mycophenolate mofetil and croscarmellose sodium are cooled to a temperature below about 60° C.

\* \* \* \* \*